United States Patent [19]
Nason et al.

[11] Patent Number: 5,637,095
[45] Date of Patent: Jun. 10, 1997

[54] MEDICATION INFUSION PUMP WITH FLEXIBLE DRIVE PLUNGER

[75] Inventors: Clyde K. Nason, Valencia; John H. Livingston, Los Angeles; Nannette M. Schnabel, Valencia, all of Calif.

[73] Assignee: Minimed Inc., Sylmar, Calif.

[21] Appl. No.: 372,367

[22] Filed: Jan. 13, 1995

[51] Int. Cl.[6] .................................................. A61M 5/20
[52] U.S. Cl. ............................ 604/135; 604/154; 604/224
[58] Field of Search .................................... 604/135, 154, 604/155, 134, 151, 152, 153; 128/DIG. 12

[56] References Cited

U.S. PATENT DOCUMENTS

| | | | |
|---|---|---|---|
| 4,276,878 | 7/1981 | Storz | 128/218 |
| 4,298,000 | 11/1981 | Thill | 604/135 |
| 4,313,439 | 2/1982 | Bubb | 604/135 |
| 4,381,006 | 4/1983 | Genese | 604/135 |
| 4,493,704 | 1/1985 | Beard et al. | 604/154 |
| 4,676,122 | 6/1987 | Szabo | 604/135 |
| 5,064,098 | 11/1991 | Hutter, III et al. | 222/137 |

FOREIGN PATENT DOCUMENTS

| | | |
|---|---|---|
| 188449 | 9/1907 | Germany. |
| 3513880A1 | 10/1986 | Germany. |

*Primary Examiner*—Michael A. Brown
*Attorney, Agent, or Firm*—Kelly Bauersfeld & Lowry

[57] ABSTRACT

A medication infusion pump is provided for controlled delivery of medication to a patient, wherein the pump includes a space-efficient flexible drive plunger for advancing a piston within a medication-containing syringe or cartridge for administration of the medication to a patient. The infusion pump comprises a compact housing defining a syringe chamber for receiving and supporting the barrel of a medication-containing syringe or cartridge having a nose end adapted for luer connection to catheter tubing through which the medication is delivered to the patient. An open rear end of the syringe barrel carries a piston which can be advanced in a controlled manner to dispense the medication. In the preferred form, the flexible drive plunger comprises a spring tape with a free end adapted for removable connection to the piston. The spring tape extends within the pump housing through a space-efficient curved path and is associated with a pump drive motor for advancing the piston within the syringe barrel to deliver the medication to the patient.

9 Claims, 3 Drawing Sheets

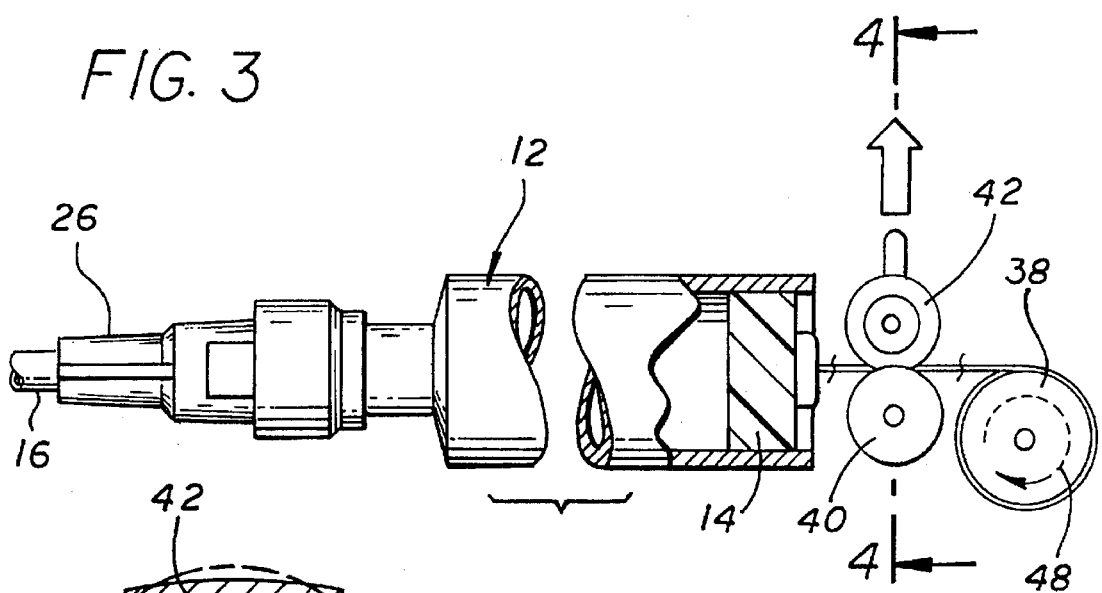
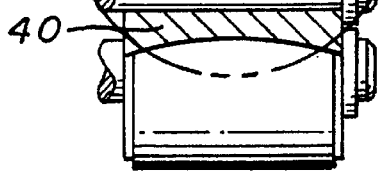
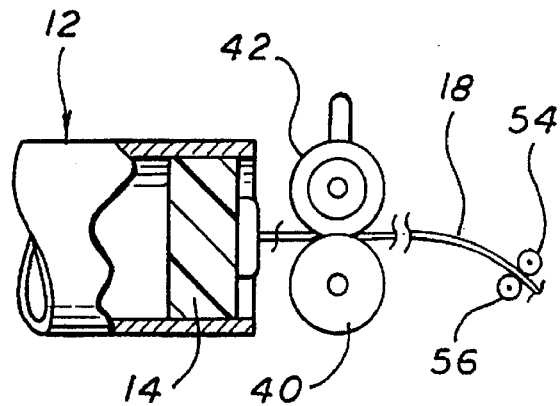
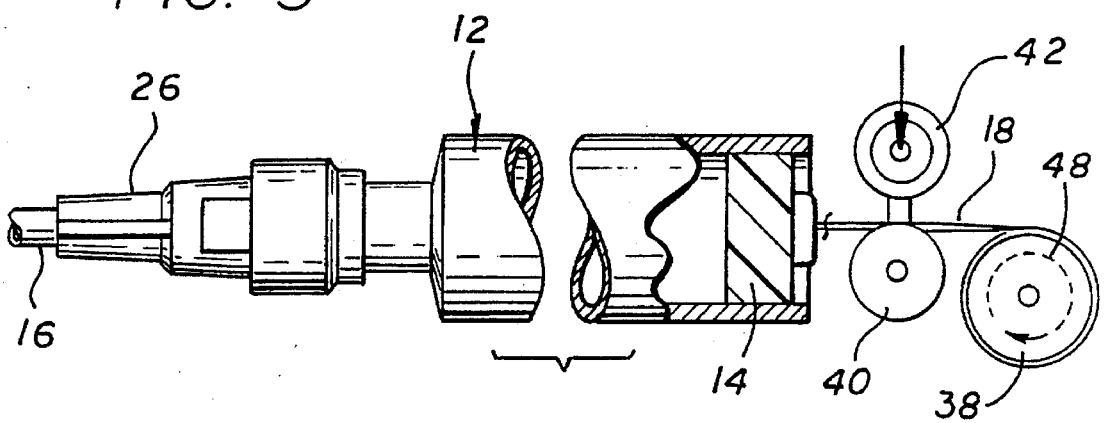

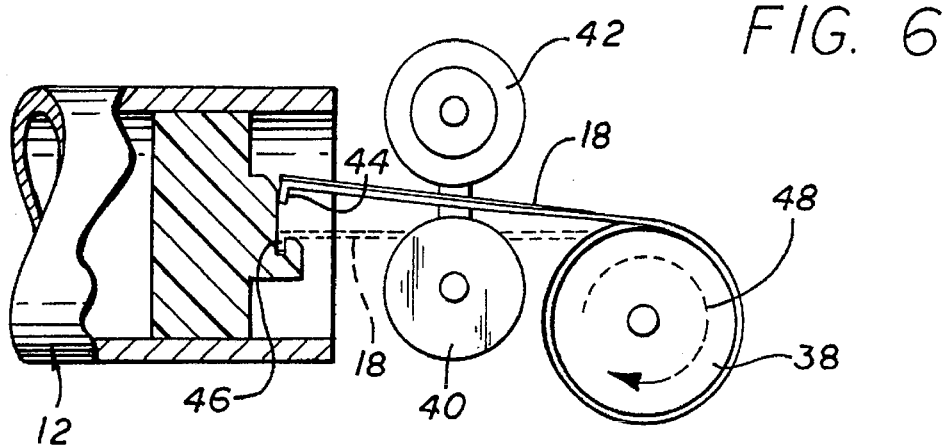
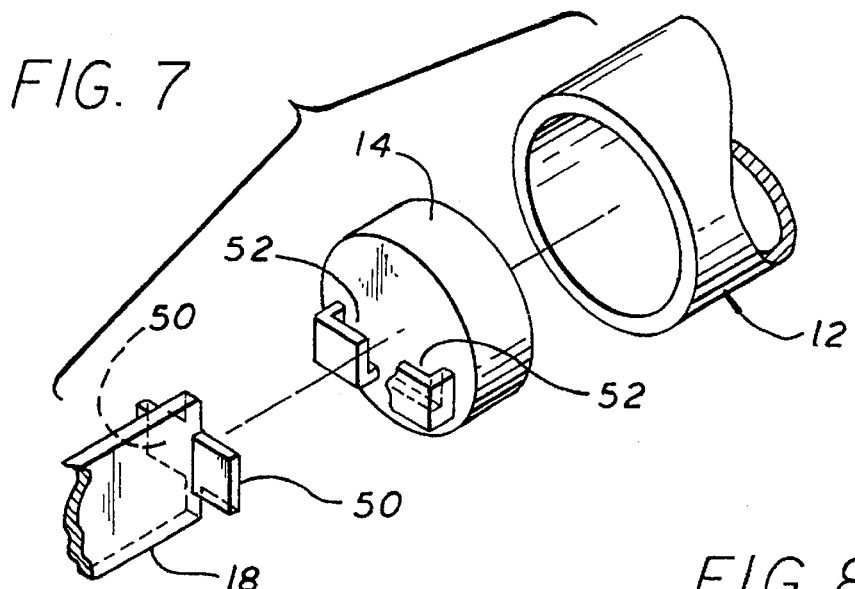
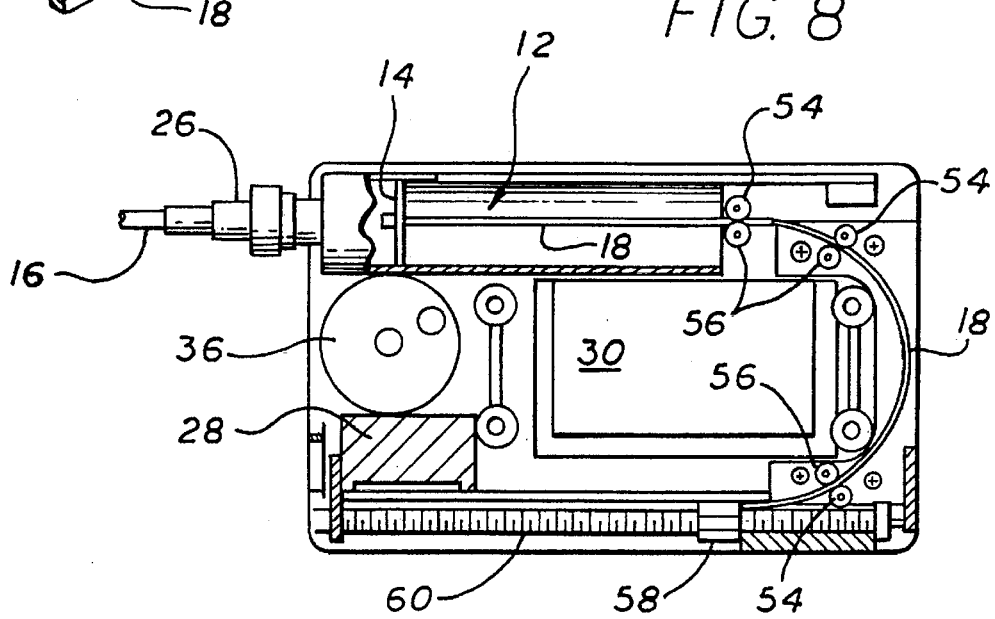

MEDICATION INFUSION PUMP WITH FLEXIBLE DRIVE PLUNGER

BACKGROUND OF THE INVENTION

This invention relates generally to improvements in infusion pumps of the type used for controlled delivery of medication to a patient. More specifically, this invention relates to an improved medication infusion pump having a modified and space-efficient flexible drive member.

Infusion pump devices and systems are relatively well-known in the medical arts, for use in delivering or dispensing a prescribed medication such as insulin to a patient. In one form, such devices comprise a relatively compact pump housing adapted to receive a syringe carrying a prescribed medication for administration to the patient through infusion tubing and an associated catheter or the like. The infusion pump includes a small drive motor connected via a lead screw assembly or the like for motor-driven advancement of a syringe piston plunger to administer the medication to the patient. Programmable control means are normally provided for operating the drive motor continuously or at periodic intervals to obtain a closely controlled and accurate delivery of the medication over an extended period of time. Such infusion pumps are utilized to administer insulin and other medications, with exemplary pump constructions being shown and described in U.S. Pat. Nos. 4,562,751; 4,678,408; 4,685,903; 4,562,751; 4,678,408; 4,685,903; 5,080,653; and 5,097,122, which are incorporated by reference herein. Moreover, such infusion pumps are available from MiniMed Technologies of Sylmar, Calif. under Model Nos. 504 and 506.

Infusion pumps of the general type described above have provided significant advantages and benefits with respect to accurate delivery of medication over an extended period of time. The infusion pump is often designed to be extremely compact and may thus be adapted to be carried by the patient, for example, by means of a belt clip or the like. As a result, important medication can be delivered to the patient with precision and in an automated manner, without significant restriction on the patient's mobility or life-style.

In the past, the physical size of the medication in fusion pump and/or the medication-carrying capacity of the pump has been a function of the length of the medication-containing syringe with the piston plunger thereof in a fully retracted state. The pump drive motor engages and advances the piston plunger slowly on a continuous or incremental basis, such that the effective length of the syringe and plunger gradually decreases as the medication is delivered to the patient. To achieve a desirably compact pump design which is both convenient and inobtrusive to the patient, the medication-carrying capacity of the syringe has been limited to relatively small volumes. It has not been possible to increase the available volume of medication in a compact pump profile without undesirably increasing the physical size of the infusion pump.

There exists, therefore, a significant need for improvements to medication infusion pumps, particularly with respect to reducing the size of the pump device without reducing the medication-carrying capacity. In the alternative, there exists a significant need for an improved medication infusion pump with an increased medication-carrying capacity without a corresponding increase in the size of the pump device. The present invention fulfills these needs and provides further related advantages.

SUMMARY OF THE INVENTION

In accordance with the invention, an improved medication infusion pump is provided with a flexible drive member for engaging and advancing a sliding piston within the barrel of medication-containing syringe or cartridge to deliver medication to a patient. The flexible drive member extends within the pump through a space-efficient curved path, and is associated with a pump drive motor for engaging and advancing the piston. Use of the flexible drive member permits the medication-carrying capacity of the pump to be substantially increased without requiring an increase in pump size, or alternately permits a substantial reduction in pump size without requiring a reduction in medication-carrying capacity.

The medication infusion pump includes a compact pump housing defining a syringe chamber for receiving and supporting the barrel of the medication-containing syringe or cartridge. A nose end of the barrel is supported for luer connection to a length of infusion tubing which can be coupled in turn via a suitable catheter to a patient. A rear or aft end of the barrel is open and carries the sliding piston in a rearwardly exposed position.

The flexible drive member comprises, in the preferred form, a length of spring tape which may be formed from spring steel to have a curved cross sectional shape when oriented in linear configuration. The spring tape is mounted within the pump housing to extend through the space-efficient curved path with one end adapted for removable connection to the sliding piston within the medication-containing barrel. In one preferred form of the invention, the spring tape is wrapped or coiled onto a take-up spool within the pump housing. Drive means such as a drive capstan roller and associated pinch roller engage and advance the spring tape under control of the pump drive motor to correspondingly engage and advance the piston to deliver medication to the patient in a programmed manner. In the linear configuration, the spring tape has sufficient longitudinal or columnar stiffness to provide an effective drive plunger for the syringe.

In one alternative preferred form of the invention, the spring tape extends through the space-efficient curved path from the medication-containing barrel to a pump drive element, such as a lead screw nut carried on an elongated lead screw. The pump drive motor rotatably drives the lead screw in a manner to advance the lead screw nut to correspondingly advance the sliding piston and thereby administer the medication to the patient. In another preferred form, the spring tape is driven by drive capstan and pinch roller, with a length of the spring tape loosely suspended and guidably received within a curved path at one side of the drive means.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is an enlarged fragmented elevation view similar to a portion of FIG. 2, and showing the flexible drive plunger and related drive means in accordance with the invention;

FIG. 4 is a sectional view taken generally on the line 4—4 of FIG. 3;

FIG. 5 is an elevation view similar to FIG. 3, but showing a pinch roller in a retracted or open position;

FIG. 6 is an enlarged fragmented elevation view similar to a portion of FIG. 5, but depicting a releasable connection between the flexible drive plunger and the piston of a medication-containing syringe;

FIG. 7 is an exploded perspective view illustrating an alternative releasable connection between the flexible drive plunger and the syringe piston;

FIG. 8 is a rear elevation view similar to FIG. 3 but showing one alternative preferred form of the invention; and FIG. 9 is a fragmented elevational view, similar to a portion of FIG. 3, and depicting another alternative preferred form of the invention.

DETAIL DESCRIPTION OF THE PREFERRED EMBODIMENTS

Figure 1:
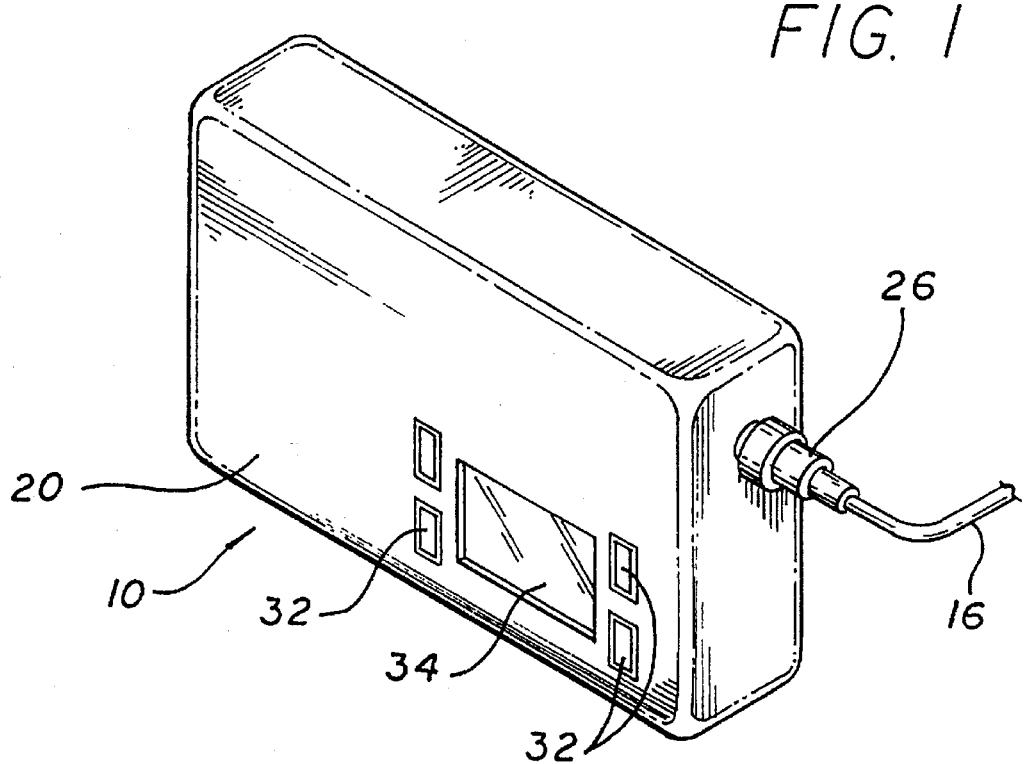
FIG. 1 is a perspective view of a compact medication infusion pump which may be equipped with a flexible drive plunger in accordance with the novel features of the invention.

As shown in the exemplary drawings, a medication infusion pump referred to generally in FIG. 1 by the reference numeral 10 is provided for controlled administration of medication to a patient. The infusion pump 10 receives and supports a barrel 12 of a medication-containing syringe or cartridge (FIG. 2), and includes means for automatically and programmably advancing a sliding piston 14 within the barrel 12 to deliver the medication through infusion tubing 16 or the like to the patient. In accordance with the invention, the infusion pump 10 includes a flexible drive member 18 for engaging and advancing the sliding piston 14.

Figure 2:
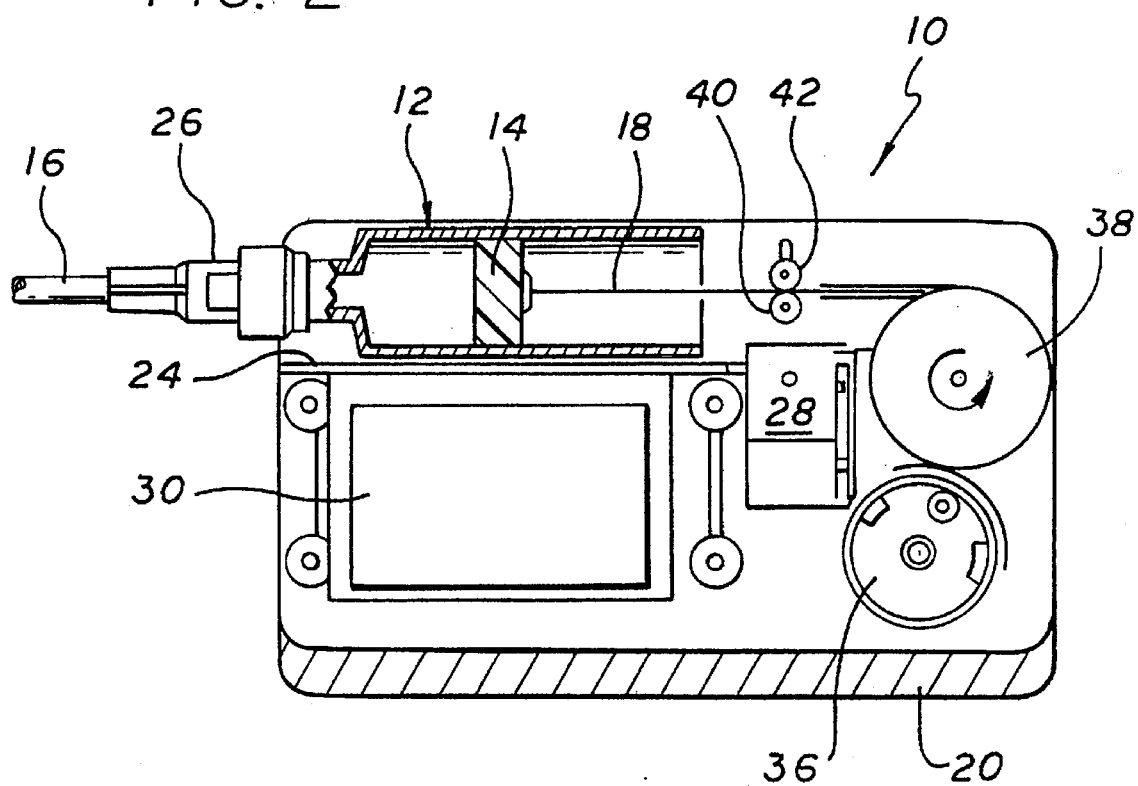
FIG. 2 is a rear elevation view of the pump of FIG. 1, with a rear housing panel removed to reveal internal operating components.

The infusion pump 10 shown in FIGS. 1 and 2 has an overall construction and operation which is generally known in the art. More specifically, as shown, the infusion pump 10 comprises a relatively compact pump housing 20 having a pivotal access door (not shown) on the rear side thereof to expose and permit access to a syringe chamber 24 (FIG. 2). The syringe chamber 24 has a size and shape to receive and support the syringe barrel 12 which is preloaded with a selected medication, such as insulin, to be administered to a patient. The medication-containing barrel 12 is supported within the syringe chamber so that a nose end thereof is positioned for convenient connection via a luer fitting 26 or the like to the infusion tubing 16. As is known in the art, the infusion tubing 26 is adapted in turn for connection with the patient by means of a suitable infusion catheter (not shown) or the like.

The infusion pump 10 additionally includes a compact drive motor 28 mounted within the housing 20 and coupled by the flexible drive member 18 to the sliding piston 14 for delivering the medication to patient, as will be described. The illustrative drive motor 28 has a mechanical output responsive to a programmable controller 30, wherein the controller 30 can be set by the attending physician or other appropriate personnel by use of an array of buttons or switches 32 (FIG. 1) with a corresponding display panel 34 on the front of the pump housing 20. As is known in the art, the programmable controller 30 and the drive motor 28 are powered by a battery 36 or the like.

In accordance with the present invention, the flexible drive member 18 mechanically couples the output of the drive motor 28 to the sliding piston 14 for delivering the medication to the patient in the desired programmed manner. As shown in FIGS. 2–4, the flexible drive member 18 extends within the pump housing 20 along a curved path, thereby providing a space-efficient construction which permits the medication-carrying capacity of the barrel 12 to be increased without increasing the size of pump housing 20, or in the alternative permits the size of the pump housing to be decreased without decreasing the volumetric capacity of the medication-containing barrel 12.

More specifically, with respect to one preferred form of the invention, the flexible drive member 18 comprises a length of spring tape having a normal cross-sectional shape of curved geometry in a longitudinally extending, substantially unstressed condition. Although the tape material may vary, a spring steel tape is presently preferred. The spring tape is shown in FIG. 2 wrapped around a take-up spool 38 within the pump housing 20, wherein the tape assumes a substantially flat or rectangular cross sectional shape when wrapped onto the spool 38. The spring tape extends from the take-up spool between a drive capstan roller 40 and a mated pinch roller 42 disposed at the rear end of the syringe chamber 24, generally in alignment with a centerline of the medication-containing barrel 12. The spring tape 18 extends further to the barrel 12, for connection of a distal or free end of the spring tape 18 to the syringe piston 14.

As shown in FIG. 4, the capstan and pinch rollers 40, 42 have a contoured profile to engage the curved cross section of the tape 18 which is unwrapped from the take-up spool 38. In the preferred geometry, the capstan and pinch rollers 40, 42 are shaped to engage the spring tap 18 with substantially line contact at or near the opposite side edges of the tape, with middle portions of the rollers 40, 42 being slightly relieved as shown. Alternately, these rollers 40, 42 may be shaped for substantially line contact at a median point of the spring tape, or for full surface engagement across the entire tape width.

The drive motor 28 is suitably coupled to the capstan roller 40 to rotatably drive said capstan roller to advance the tape 18 toward the barrel 12 of the medication-containing syringe. The flexible tape 18 extends from the capstan roller 40 to the piston 14 with a generally linear configuration, wherein the linear tape has sufficient longitudinal stiffness to act as a rigid column to form an effective plunger for the piston 14 to administer the medication through the tubing 16 to the patient. However, the tape 18 has sufficient flexibility to wrap onto the spool 38, whereby the tape occupies minimal space when retracted to accommodate a fully loaded syringe. Alternative tape drive engagements may be used, such as connection of the drive motor 28 to rotatably drive the spool 38.

FIGS. 5 and 6 show one preferred releasable connection between the free end of the spring tape 18 and the syringe piston 14, wherein the pinch roller 42 is retractable relative to the capstan roller 40 to permit the tape 18 to be inserted into or removed from the space between these rollers. In this regard, the pinch roller 42 can be adapted for two-position movement between the drive position shown in FIGS. 3 and 4, and the open position shown in FIGS. 5 and 6. A downturned tab or foot 44 is carried at the free end of the tape 18 for seated reception into a slot 46 formed at the back side of the piston 14. A suitable torsion spring referenced in FIGS. 3, 5 and 6 by arrow 48 may be provided with the take-up spool 38 to re-wind the tape 18 thereon when the tape is released from the piston 14 while the pinch roller 42 is in the retracted position.

In operation, when the medication-containing barrel 12 is loaded into the pump housing 20, the pinch roller 42 is retracted to permit connection of the spring tape to the piston 42. The pinch roller 42 is then returned to the normal drive position. The controller 30 is operated to prime the pump for operation, and thereafter to operate the drive motor 28 in a manner rotating the drive capstan roller 40 to advance the spring tape 18 into the syringe chamber 24 in a controlled manner. Operation of the capstan roller results in linear advancement of the piston 14 within the barrel 12, and corresponding delivery of the medication to the patient. Importantly, the connection between the spring tape and the piston 14 prevents undesired forward or rearward piston displacement within the barrel 12, which might otherwise occur in response to fluid pressures applied to the medication within the syringe barrel.

FIG. 7 shows an alternative spring tape construction for releasable connection to the piston 14 of a medication-containing syringe. As shown, the free end of the spring tape 18 may include a pair of oppositely projecting tabs 50 for seated reception into a corresponding pair of laterally open slots 52 defined at a rear side of the piston 14. As described with respect to FIGS. 2–6, tape connection to and disconnection from the piston 14 is easily accomplished with the pinch roller 42 in a retracted position.

FIG. 8 shows a further alternative preferred form of the invention, wherein components corresponding with those previously described with respect to FIGS. 1–6 are identified by common reference numerals. In this alternative embodiment, the spring tape 18 is again adapted for removable connection to the sliding piston 14 of the medication-containing barrel 12 within the syringe chamber 24. The spring tape 18 extends from the syringe chamber 24 through a space-efficient curved path in association with a series of guide roller pairs 54, 56 to an opposite end wherein the spring tape is connected to a lead screw nut 58 carried on a lead screw 60. The drive motor 28 provides a rotary output for rotatably driving the lead screw 60 in a manner advancing the lead screw nut 58 along the lead screw. Such linear displacement of the lead screw nut 58 translates or shifts the spring tape 18 along its curved path. The segment or portion of the tape extending between the last set of guide rollers 54, 56 and the piston 14 is generally linear, whereby the spring tape 18 functions as a longitudinally stiff plunger to advance the sliding piston 14 within the medication containing barrel 12. As a result, the medication is again programmably administered to the patient.

FIG. 9 depicts another alternative preferred form of this invention, wherein a drive means including a drive capstan 40 and pinch roller 42 according to FIGS. 2–5 are used to advance the spring tape 18 into the syringe barrel to dispense medication. In this version, a length of the spring tape is loosely suspended within the pump housing at one side of the rollers 40, 42, opposite to the syringe 12. This loosely suspended portion may extend through a space-efficient curved path, and guide rollers 54, 56 similar to those shown in FIG. 8 may be used to guide the suspended tape portion through the curved path.

The present invention thus provides a highly compact medication infusion pump with a flexible drive member which extends through a space-efficient curved path. However, a segment of the flexible drive member adjacent to the syringe piston 15 is linearly oriented and provides sufficient columnar stiffness to act as an effective piston plunger. With this arrangement, the medication-containing capacity of the pump 10 can be significantly increased without increasing pump size, or in the alternative, the overall size of the pump can be significantly decreased without reducing the volumetric medication capacity.

A variety of further modifications and improvements to the present invention will be apparent to those skilled in the art. Accordingly, no limitation on the invention is intended by way of the foregoing description and accompanying drawings, except as set forth in the appended claims.

What is claimed is:

1. A medication infusion pump, comprising:

a pump housing defining a syringe chamber for receiving and supporting a syringe barrel having a selected medication therein and a sliding piston within said barrel for advancement therein to administer the medication to a patient;

a pump drive motor;

a flexible drive member operably connected between said syringe piston and said drive motor, said flexible drive member having at least a portion thereof extending within said housing through a curved path, and said flexible drive member having sufficient longitudinal stiffness to advance said piston within said barrel in response to operation of said drive motor and;

a take-up spool within said housing and having said flexible drive member wound thereon, said drive motor including means for unwinding said flexible drive member from said take-up spool, said drive motor including a drive capstan roller and a pinch roller with said flexible drive member passing therebetween, said drive capstan roller being rotatably driven to advance said flexible drive member toward the syringe piston.

2. The medication infusion pump of claim 1 wherein said flexible drive member comprises a spring tape.

3. The medication infusion pump of claim 2 wherein said spring tape has a curved cross sectional shape when said spring tape is oriented in an unstressed, substantially linear longitudinal configuration.

4. The medication infusion pump of claim 1 wherein said take-up spool includes spring means for normally rotating said spool in a direction to wind said flexible drive member onto said spool.

5. The medication infusion pump of claim 1 wherein one of said drive capstan and pinch rollers is retractable relative to the other to permit said flexible drive member to be inserted and removed therebetween.

6. The medication infusion pump of claim 1 wherein said flexible drive member extends generally linearly between said spring piston and said drive capstan and pinch rollers.

7. The medication infusion pump of claim 1 wherein said flexible drive member has a free end with means thereon for releasable connection to said syringe piston.

8. The medication infusion pump of claim 1 further including means for orienting a portion of said flexible drive member disposed adjacent to said syringe piston in a generally linearly extending configuration.

9. The medication infusion pump of claim 1 wherein further including a lead screw rotatably driven by said drive motor, and a lead screw nut on said lead screw, said flexible drive member extending along said curved path between said lead screw nut and said syringe piston.

* * * * *